United States Patent [19]
Van Lommen et al.

[11] Patent Number: 5,990,123
[45] Date of Patent: Nov. 23, 1999

[54] VASOCONSTRICTIVE SUBSTITUTED 2,3-DIHYDRO-1,4-DIOXINOPYRIDINES

[75] Inventors: Guy Rosalia Eugène Van Lommen, Berlaar, Belgium; José Ignacio Andrés-Gil, Madrid, Spain; Francisco Javier Fernández-Gadea; Maria Encarnacion Matesanz-Ballesteros, both of Toledo, Spain

[73] Assignee: Janssen Pharmaceutica, N.V., Beerse, Belgium

[21] Appl. No.: 08/875,835

[22] PCT Filed: Jan. 30, 1996

[86] PCT No.: PCT/EP96/00396

§ 371 Date: Aug. 6, 1997

§ 102(e) Date: Aug. 6, 1997

[87] PCT Pub. No.: WO96/24596

PCT Pub. Date: Aug. 15, 1996

[30] Foreign Application Priority Data

Feb. 7, 1995 [EP] European Pat. Off. .............. 95 20 290

[51] Int. Cl.$^6$ ....................... C07D 491/04; A61K 31/435
[52] U.S. Cl. ............................. 514/302; 546/115
[58] Field of Search ............... 546/115; 514/302

[56] References Cited

FOREIGN PATENT DOCUMENTS 0 559 285  9/1993  European Pat. Off. .
42 26 527  2/1994  European Pat. Off. .

OTHER PUBLICATIONS

International Search Report Application No. PCT/EP96/00396, May 1996.
International Preliminary Examination Report Application No. , Nov. 1996 PCT/EP96/00396.

*Primary Examiner*—Zinna Northington Davis
*Attorney, Agent, or Firm*—Mary A. Appollina

[57] ABSTRACT

The present invention is concerned with compounds of formula

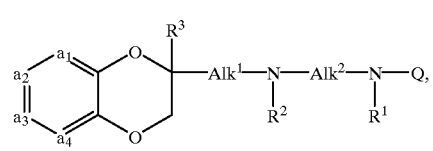

(I)

the N-oxide forms, the pharmaceutically acceptable acid addition salts and the stereochemically isomeric forms thereof, wherein $=a_1-a_2=a_3-a_4=$ is a bivalent radical of formula $=N-CH=CH-CH=$ (a), $=CH-N=CH-CH=$ (b), $=CH-CH=N-CH=$ (c), $=CH-CH=CH-N=$ (d), wherein one or two hydrogen atoms can be substituted by halo, hydroxy, $C_{1-6}$alkyl or $C_{1-6}$alkyloxy; $R^1$ is hydrogen or $C_{1-6}$alkyl; $R^2$ is hydrogen or $C_{1-6}$alkyl; $R^3$ is hydrogen or $C_{1-6}$alkyl; $Alk^1$ is $C_{1-5}$alkanediyl; $Alk^2$ is $C_{2-15}$alkanediyl; Q is a five- or six-membered heterocyclic ring containing at least one nitrogen atom or a radical of formula $-C(NR^5R^6)=C-R^4$ wherein $R^4$ is hydrogen, cyano, aminocarbonyl or $C_{1-6}$alkyl; $R^5$ is hydrogen, $C_{1-6}$alkyl, $C_{3-6}$alkenyl or $C_{3-6}$alkynyl; $R^6$ is hydrogen or $C_{1-6}$alkyl; or $R^5$ and $R^6$ taken together may form a bivalent radical of formula $-(CH_2)_4-$ or $-(CH_2)_5-$.

Pharmaceutical compositions, preparations and use as a medicine are described.

14 Claims, No Drawings

VASOCONSTRICTIVE SUBSTITUTED 2,3-DIHYDRO-1,4-DIOXINOPYRIDINES

CROSS-REFERENCE TO RELATED APPLICATIONS

This application is based upon PCT Application Ser. No. PCT/EP 96/00396, filed Jan. 30, 1996, which claims priority from European Patent Application Ser. No. 95.200.290.5, filed on Feb. 7, 1995.

The present invention relates to novel substituted 2,3-dihydro-1,4-dioxinopyridines, processes for their preparations, pharmaceutical compositions containing them and their use as a medicine, in particular for the prevention or treatment of disorders characterized by excessive vasodilatation, especially migraine.

Migraine is a non-lethal disease suffered by one in ten individuals. The main symptom is headache; other symptoms include vomiting and photophobia. For many years the most widely used treatment for migraine involved the administration of ergotalkaloids, which show however several adverse side effects. Recently a tryptamine derivative, i.e. sumatriptan, was introduced as a novel antimigraine drug. We have now surprisingly found that the present novel substituted 2,3-dihydro-1,4-dioxinopyridines show $5-HT_1$-like agonistic activity and can thus be used in the treatment of disorders characterized by excessive vasodilatation, especially migraine.

EP-A-0,559,285, published on Sep. 8, 1993, discloses 1,4-dioxino[2,3-b]pyridine derivatives as strong serotonine ligands with preference for the $5-HT_{1A}$ receptor useful as antidepressants or as anti-anxiety agents.

The present invention is concerned with compounds of formula

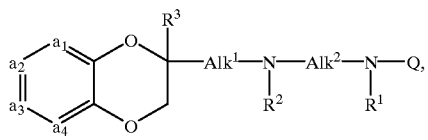

(I)

the N-oxide forms, the pharmaceutically acceptable acid addition salts and the stereochemically isomeric forms thereof, wherein $=a_1-a_2=a_3-a_4=$ is a bivalent radical of formula:

 (a),

 (b),

 (c),

 (d), wherein one or two hydrogen atoms can be substituted by halo, hydroxy, $C_{1-6}$alkyl or $C_{1-6}$alkyloxy;

$R^1$, $R^2$ and $R^3$ each independently are hydrogen or $C_{1-6}$alkyl;

$Alk^1$ is $C_{1-5}$alkanediyl;

$Alk^2$ is $C_{2-15}$alkanediyl;

Q is a radical of formula

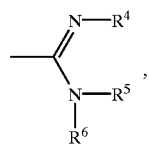 (aa)

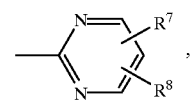 (bb)

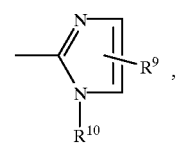 (cc)

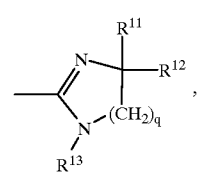 (dd)

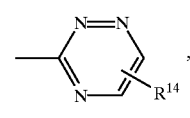 (ee)

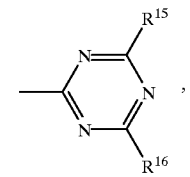 (ff)

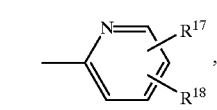 (gg)

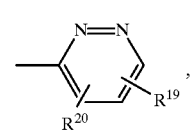 (hh)

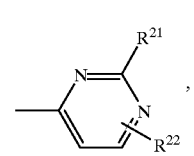 (ii)

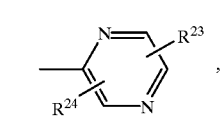 (jj)

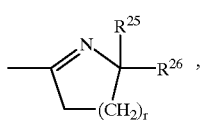

(kk)

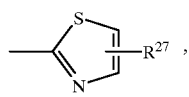

(ll)

wherein
$R^4$ is hydrogen, cyano, aminocarbonyl or $C_{1-6}$alkyl;
$R^5$ is hydrogen, $C_{1-6}$alkyl, $C_{3-6}$alkenyl or $C_{3-6}$alkynyl;
$R^6$ is hydrogen or $C_{1-6}$alkyl; or
$R^5$ and $R^6$ taken together may form a bivalent radical of formula —$(CH_2)_4$— or —$(CH_2)_5$—;
$R^7$ and $R^8$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;
$R^9$ is hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, amino-carbonyl, $C_{1-6}$alkyloxycarbonylamino, $C_{1-6}$alkylaminocarbonylamino, piperidinyl, pyrrolidinyl;
$R^{10}$is hydrogen, $C_{1-6}$alkyl, $C_{1-6}$alkylcarbonyl, or aryl $C_{1-6}$alkyl;
$R^{11}$ and $R^{12}$ are hydrogen or taken together with the carbon atom to which they are connected form C(O);
q is 1 or 2;
$R^{13}$ is hydrogen, $C_{1-6}$alkyl, $C_{1-6}$alkylcarbonyl, or aryl $C_{1-6}$alkyl;
$R^{14}$ is hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;
$R^{15}$ and $R^{16}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;
$R^{17}$ and $R^{18}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;
$R^{19}$ and $R^{20}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;
$R^{21}$ and $R^{22}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;
$R^{23}$ and $R^{24}$ each independently are hydrogen, hydroxy, halo, $C_{1-6}$alkyl, $C_{1-6}$alkyloxy, aryloxy, $C_{1-6}$alkylthio, cyano, amino, mono- or di($C_{1-6}$alkyl)amino, mono- or di($C_{3-6}$cycloalkyl)amino, aminocarbonyl, $C_{1-6}$alkyloxycarbonylamino, $C_{1-6}$alkylaminocarbonylamino, piperidinyl, pyrrolidinyl;
r is 1 or 2;
$R^{25}$ and $R^{26}$ are hydrogen or taken together with the carbon atom to which they are connected form a C(O);
$R^{27}$ is hydrogen, halo or $C_{1-6}$alkyl, and aryl is phenyl optionally substituted with halo, hydroxy, $C_{1-6}$alkyl or $C_{1-6}$alkyloxy.

Some of the compounds of formula (I) may also exist in their tautomeric forms. Such forms although not explicitly indicated in the above formula are intended to be included within the scope of the present invention.

As used in the foregoing definitions halo defines fluoro, chloro, bromo and iodo; $C_{1-6}$alkyl defines straight and branch chained saturated hydrocarbon radicals having from 1 to 6 carbon atoms such as, for example, methyl, ethyl, propyl, butyl, pentyl, hexyl and the like; $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated, $C_{3-6}$alkynyl defines straight and branch chained hydrocarbon radicals containing one triple bond and having from 3 to 6 carbon atoms such as, for example, 2-propynyl, 3-butynyl, 2-butynyl, 2-pentynyl, 3-pentynyl, 3-hexynyl, and the like; and the carbon atom of said $C_{3-6}$alkynylradical being connected to a nitrogen atom preferably is saturated; $C_{3-6}$cycloalkyl is generic to cyclopropyl, cyclobutyl, cyclopentyl and cyclohexyl; $C_{1-5}$alkanediyl defines bivalent straight and branch chained saturated hydrocarbon radicals having form 1 to 5 carbon atoms, such as, for example, methylene, 1,2-ethanediyl, 1,3-propanediyl, 1,4-butanediyl, 1,5-pentanediyl and the branched isomers thereof; $C_{2-15}$alkanediyl defines bivalent straight and branch chained saturated hydrocarbon radicals having from 2 to 15 carbon atoms such as, for example, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, 1,13-tridecanediyl, 1,14-tetradecanediyl, 1,15-pentadecanediyl and the branched isomers thereof. The term "C(O)" refers to a carbonyl group.

The pharmaceutically acceptable acid addition salts as mentioned hereinabove are meant to comprise the acid addition salt forms which can conveniently be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely, said acid addition salt forms can be converted in the free base forms by treatment with an appropriate base.

The term addition salt also comprises the hydrates and solvent addition forms which the compounds of formula (I) are able to form. Examples of such forms are e.g. hydrates, alcoholates and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; and $C_{3-6}$-alkenyl radicals may have the E- or Z-configuration. Stereochemically isomeric forms of the compounds of formula (I) are intended to be embraced within the scope of this invention.

The radical "=$a_1$—$a_2$=$a_3$—$a_4$=" is suitably a radical of formula (a) or (d);

$R^1$ is suitably methyl or hydrogen, preferably $R^1$ is hydrogen;

$R^2$ is suitably methyl or hydrogen, preferably $R^2$ is hydrogen;

$R^3$ is suitably methyl or hydrogen, preferably $R^3$ is hydrogen;

$Alk^1$ is suitably $C_{1-3}$alkanediyl, preferably $Alk^1$ is methylene;

$Alk^2$ is suitably $C_{2-6}$alkanediyl, preferably $Alk^2$ is 1,3-propanediyl;

Q is preferably a radical of formula (bb) or (hh);

$R^7$ and $R^8$ each independently are suitably hydrogen, hydroxy, halo or methyl, preferably both $R^7$ and $R^8$ are hydrogen;

$R^{19}$ and $R^{20}$ each independently suitably are hydrogen, hydroxy, halo or methyl, preferably $R^{19}$ is hydrogen and $R^{20}$ is chloro.

Interesting compounds are those compounds of formula (I), wherein $R^1$ and $R^2$ both are hydrogen.

Also interesting compounds are those compounds of formula (I), wherein =$a_1$—$a_2$=$a_3$—$a_4$= is a bivalent radical of formula (a).

Another goup of interesting compounds are those compounds of formula (I), wherein =$a_1$—$a_2$=$a_3$—$a_4$= is a bivalent radical of formula (d).

Particular compounds are those interesting compounds of formula (I), wherein Q is a radical of formula (bb) or (hh), especially (bb).

Particularly interesting compounds are those interesting compounds, wherein Q is a radical of formula (bb), $R^7$ and $R^8$ are both hydrogen.

Preferred compounds are:

N-[(2,3-dihydro-1,4-dioxino[2,3-b]pyridin-3-yl)methyl]-N'-2-pyrimidinyl-1,3-propanediamine;

N-[(2,3-dihydro-1,4-dioxino[2,3-b]pyridin-2-yl)methyl]-N'-2-pyrimidinyl-1,3-propanediamine;

N-(6-chloro-3-pyridazinyl)-N'-[(2,3-dihydro-1,4-dioxino[2,3-b]pyridin-2-yl)methyl]-1,3-propanediamine; the pharmaceutically acceptable acid addition salts or the stereochemically isomeric forms thereof.

The compounds of formula (I) can generally be prepared by N-alkylating an amine of formula (II) with an intermediate of formula (III), wherein $W^2$ is a reactive leaving group such as, for example, a halogen, methanesulfonyloxy or toluenesulfonyloxy, optionally in appropriate solvents such as, e.g. 2-butanone, tetrahydrofuran, toluene or N,N-dimethylformamide.

Stirring and heating may enhance the reaction rate. Optionally a suitable base may be added to pick up the acid that is formed during the course of the reaction such as, for example, sodium or potassium carbonate, sodium or potassium hydrogen carbonate, N,N-diethylethanamine or pyridine.

The compounds of formula (I) may also be prepared by reacting a diamine of formula (IV) with a reagent of formula (V). In the formulas (IV), (V) and all the following formulas the variabels "=$a_1$—$a_2$=$a_3$—$a_4$=", $R^1$, $R^2$, $R^3$, $Alk^1$, $Alk^2$, and Q are as defined under formula (I). In formula (V) $W^1$ is a reactive leaving group such as, for example, a halogen, methoxy, ethoxy, phenoxy, methylthio, ethylthio or benzenethio.

Said reaction can be performed by stirring the diamine of formula (IV) with the reagent of formula (V) optionally in an appropriate solvent such as, for example, ethanol, dichloromethane, tetrahydrofuran, toluene or mixtures thereof. Optionally a base, such as, for example, sodium or potassium carbonate, sodium or potassium hydrogen carbonate, N,N-diethylethanamine or pyridine, can be added to pick up the acid that may be formed during the course of the reaction. Preferably the reaction is performed at the reflux temperature of the reaction mixture.

The compounds of formula (I) may also be prepared by reductive N-alkylation of an aminoderivative of formula (VIII) with an appropriate aldehyde of formula (VII), wherein $Alk^3$ is a direct bond or $C_{1-4}$alkanediyl.

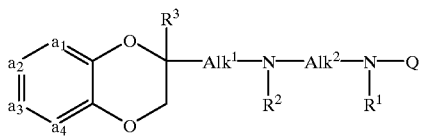

(I)

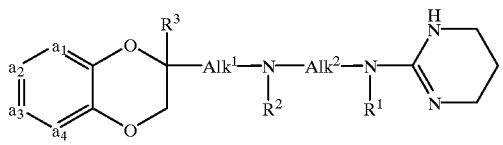

(X)

Said reaction is performed by stirring the reactants in an appropriate solvent such as, for example, ethanol, tetrahydrofuran, toluene or mixtures thereof. Optionally a water separator can be used to remove the water that is formed during the course of the reaction. The resulting imine can then be reduced by reactive hydride reagents such as, for example, sodium borohydride, or by catalytic hydrogenation on an appropriate catalyst, such as, for example palladium on charcoal, platinum on charcoal, Raney nickel and the like in a suitable solvent such as, for example, methanol, tetrahydrofuran, ethyl acetate, or acetic acid. Optionally the reaction may be performed at elevated temperatures and/or pressures.

The intermediate aldehyde of formula (VII) can be prepared by reducing an acyl derivative of formula (VI) wherein $Alk^3$ is defined as above and Y is halo. The acyl halide can be prepared by reacting the acid of formula (VI) wherein Y is OH, with a halogenating reagent such as thionylchloride, phosphorus trichloride, phosphorus tribromide, oxalylchloride and the like. The latter reaction may be performed in an excess of the halogenating reagent or in appropriate solvents such as, for example, dichloromethane, toluene, tetrahydrofuran, 1,4-dioxane or N,N-dimethylformamide. Stirring and elevated temperatures may be appropriate to enhance the rate of the reaction. Said reduction of the acylhalide of formula (VI) can for instance be performed by catalytic hydrogenation with a catalyst such as palladium on charcoal, palladium on bariumsulfate, platinum on charcoal and the like in appropriate solvents such as, for example, tetrahydrofuran; preferably in admixture with a dipolar aprotic solvent, such as, for example N,N-dimethylformamide. Optionally a catalyst poison can be added, such as thiophene, quinoline/sulfur and the like. The reaction sequence starting from the intermediate of formula (VI) and yielding compounds of formula (I) may be performed as a one-pot procedure.

The compounds of formula (I), can also be converted into each other by functional group transformations. For instance the compounds of formula (I), wherein Q represents a pyrimidinyl moiety, said compounds being represented by formula (IX), can be converted into the tetrahydroanalogs of formula (X) following art-known catalytic hydrogenation procedures.

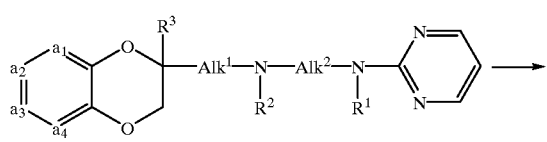

(IX)

Furthermore, compounds of formula (I) bearing a $C_{3-6}$alkynylgroup or $C_{3-6}$alkenylgroup can be converted into the corresponding compounds bearing $C_{1-6}$alkylgroup following art-known hydrogenation techniques.

Compounds of formula (I) bearing a cyanogroup can be converted into the corresponding compounds bearing an aminomethyl substituent following art-known hydrogenation techniques.

Compounds bearing an alkyloxy substituent can be converted into compounds bearing a hydroxy group by treating the alkyloxy compound with an appropriate acidic reagent such as for example, hydrohalic acid, e.g. hydrobromic acid or borontribromide and the like.

Compounds bearing an amino substituent can be N-acylated or N-alkylated following art-known N-acylation or N-alkylation procedures. The N-oxide forms of the compounds formula (I) may also be prepared following art-known methods.

Intermediates of formula (III), wherein "=$a_1$—$a_2$=$a_3$—$a_4$=" is a bivalent radical of formula a) have been described in EP-A-0,559,285.

Intermediates of formula (III), wherein "=$a_1$—$a_2$=$a_3$—$a_4$=" is a bivalent radical of formula (b) wherein one or two hydrogen atoms of the pyridine moiety can be substituted by halo, hydroxy, $C_{1-6}$alkyl or $C_{1-6}$alkyloxy, said intermediates being represented by formula (III-b), are deemed novel.

(III-b)

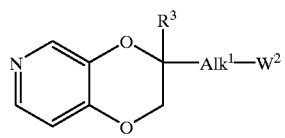

Intermediates of formula (III), wherein "=$a_1$—$a_2$=$a_3$—$a_4$=" is a bivalent radical of formula (c) wherein one or two hydrogen atoms of the pyridine moiety can be substituted by halo, hydroxy, $C_{1-6}$alkyl or $C_{1-6}$alkyloxy, said intermediates being represented by formula (III-c), are deemed novel.

(III-c)

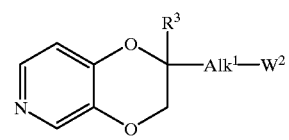

Intermediates of formula (III), wherein "=$a_1$—$a_2$=$a_3$—$a_4$=" is a bivalent radical of formula (d) have been described in Heterocycles, 36 (10), 2327 (1993).

Pure stereochemically isomeric forms of the compounds of this invention may be obtained by the application of art-known procedures. Diastereoisomers may be separated by physical separation methods such as selective crystallization and chromatographic techniques, e.g. liquid chromatography. Enantiomers may be separated from each other by the selective crystallization of their diastereomeric salts with optically active acids. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. Stereochemically isomeric forms of the compounds of formula (I) are obviously intended to be included within the scope of the invention.

The compounds of formula (I), the pharmaceutically acceptable acid addition salts and stereochemically isomeric forms thereof have interesting pharmacological properties in hat they show $5HT_1$-like agonistic activity. The compounds of the present invention have a remarkable vasoconstrictor activity. They are useful to prevent and treat conditions which are related to vasodilatation. For instance, they are useful in the treatment of conditions characterized by or associated with cephalic pain, e.g. cluster headache and headache associated with vascular disorders, especially migraine. These compounds are also useful in the treatment of venous insufficiency and in the treatment of conditions associated with hypotension.

The vasoconstrictor activity of the compounds of formula (I) can be determined using an in vitro-test as is described in "Instantaneous changes of alpha-adrenoreceptor affinity caused by moderate cooling in canine cutaneous veins" in the American Journal of Physiology 234(4), H330–H337, 1978; or in the test described in the pharmacological example, wherein the serotonin-like response of the compounds of the present invention was tested on the basilar arteries of pigs.

In view of their useful pharmacological properties, the subject compounds may be formulated into various pharmaceutical forms for administration purposes. To prepare the pharmaceutical compositions of this invention, an effective amount of a particular compound, in base form or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g. as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention therefore may be used as medicines in conditions related to vasodilatation, more in particular hypotension, venous insufficiency and especially cephalic pain among which migraine. The compounds of the present invention also provide a method of treating warm-blooded animals suffering from conditions related to vasodilatation, such as, hypotension, venous insufficiency and especially cephalic pain among which migraine by administering an effective amount of a compound of formula (I), a pharmaceutically acceptable acid addition salt or a stereoisomeric form thereof. Those skilled in the art could easily determine the effective amount from the test results presented hereinafter. In general it is contemplated that an effective daily amount would be from 1 µg/kg to 1 mg/kg body weight, and in particular from 2 µg/kg to 200 µg/kg body weight. It may be appropriate to administer the required dose as two, three, four or more sub-doses at appropriate intervals throughout the day. Said sub-doses may be formulated as unit dosage forms, for example, containing 0.005 to 20 mg, and in particular 0.1 mg to 10 mg of active ingredient per unit dosage form.

The following examples are intended to illustrate and not to limit the scope of the present invention in all its aspects.

Experimental Part

A) Preparation of the Intermediates

EXAMPLE 1

2-chloro-pyrimidine (24.3 g) was added portionwise to a mixture of 1,3-propanediamine (85 g) in toluene (240 mL) while stirring at reflux temperature. The reaction mixture was stirred and refluxed for 3 hours. The reaction mixture was cooled, the precipitate was filtered off and the filtrate was evaporated. The residue was distilled in vacuo, yielding 53 g (65.7%) of N-2-pyrimidinyl-1,3-propanediamine (intermediate 1).

EXAMPLE 2

A mixture of 3,6-dichloropyridazine (25 g), 1,3-propanediamine (62 g) and sodium carbonate (18 g) in ethanol (500 mL) was stirred and refluxed overnight. The reaction mixture was filtered over dicalite and the filtrate was evaporated. The residue was crystallized from acetonitrile. The crystals were filtered off and dried, yielding 20.7 g of N-(6-chloro-3-pyridazinyl)-1,3-propanediamine; mp. 124.9° C. (intermediate 2).

EXAMPLE 3

Methanesulfonyl chloride (1.7 mL) in dichloromethane (10 mL) was added dropwise to a mixture, cooled on an ice bath, of (±)-2-(hydroxymethyl)-2,3-dihydro-1,4-dioxino-[2,3-b]-pyridine (2.4 g), prepared as described in Heterocycles, 36 (10), 2327 (1993), and N,N-diethylethaneamine (4 mL) in dichloromethane (45 mL) and the mixture was stirred at 5° C. for 1 hour. The precipitate was filtered off and the filtrate was extracted with water. The organic layer was dried over $Na_2SO_4$, filtered and evaporated, yielding 3.54 g of (±)-2,3-dihydro-1,4-dioxino[2,3-b]pyridine-2-methanol methanesulfonate(ester) (intermediate 3).

In a similar way was prepared: (±)-2,3-dihydro-1,4-dioxino[2,3-b]pyridine-3-methanol methanesulfonate(ester) (intermediate 4).

B) Preparation of the Final Compounds

EXAMPLE 4

Intermediate 3 (3.68 g) and intermediate 2 (6.22 g) were stirred at 100° C. for 1 hour. The mixture was purified first by an open column chromatography over silica gel (eluent: $CH_2Cl_2/(CH_3OH/NH_3)$ 96/4) and then by HPLC (eluent: hexane/$CH_2Cl_2/(CH_3OH/NH_3)$ 10/9/1). The pure fractions were collected, evaporated and the residue was recrystallized from $CH_3CN$, yielding 0.77 g (12%) of (±)-N-(6-chloro-3-pyridazinyl)-N-[(2,3-dihydro-1,4-dioxino[2,3-b]pyridin-2-yl)methyl]-1,3-propane-diamine (mp. 100.8° C.; compound 1).

EXAMPLE 5

Intermediate 4 (1.98 g) and intermediate 1 (2.46 g) were stirred at 100° C. for 1 hour. The mixture was purified first by flash chromatography over silica gel (eluent: $CH_2Cl_2/CH_3OH$ 96/4, 94/6 and 90/10) and then by an other flash chromatography (eluent: $CH_2C_2/(CH_3OH/NH_3)$ 96/4). The pure fractions were collected, evaporated and the residue was converted into the ethanedioic acid salt (1:1) in ethanol, yielding 1.26 g (40%) of (±)-N-[(2,3-dihydro-1,4-dioxino[2,3-b]pyridin-3-yl)methyl]-N'-2-pyrimidinyl-1,3-propanediamine ethanedioate(1:1) (mp. 193.6° C.; compound 2).

In a similar way was prepared: (±)-N-[(2,3-dihydro-1,4-dioxino[2,3-b]pyridin-2-yl)methyl]-N'-2-pyrimidinyl-1,3-propanediamine ethanedioate(1:1) (mp. 181.2° C.; compound 3).

Pharmacological Example

EXAMPLE 6

Segments of basilar arteries taken from pigs (anaesthetised with sodium pentobarbital) were mounted for recording of isometric tension in organ baths. The preparations were bathed in Krebs-Henseleit solution. The solution was kept at 37° C. and gassed with a mixture of 95% $O_2$–5% $CO_2$. The preparations were stretched until a stable basal tension of 2 grams was obtained.

The preparations were made to constrict with serotonin ($3\times10^{-7}$ M). The response to the addition of serotonin was measured and subsequently the serotonin was washed away. This procedure was repeated until stable responses were obtained. Subsequently the test compound was administered to the organ bath and the constriction of the preparation was measured. This constrictive response was expressed as a percentage of the response to serotonin as measured previously. The lowest active concentration was defined as the concentration at which 50% of the response to serotonin is obtained.

Table 1 presents the lowest active concentrations of the compounds of formula (I).

TABLE 1

| Co. No. | lowest active concentration (M) |
| --- | --- |
| 1 | $>1 \times 10^{-6}$ |
| 2 | $1 \times 10^{-7}$ |
| 3 | $3 \times 10^{-6}$ |

E. Composition Examples

"Active ingredient" (A.I.) as used throughout these examples relates to a compound of formula (I), a pharmaceutically acceptable acid addition salt or a stereochemically isomeric form thereof.

EXAMPLE 7

Oral Drops

500 Grams of the A.I. was dissolved in 0.5 l of 2-hydroxypropanoic acid and 1.5 l of the polyethylene glycol at 60–80° C. After cooling to 30–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 8

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 9

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE 10

Film-coated Tablets

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 11

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

We claim:

1. A compound having the formula

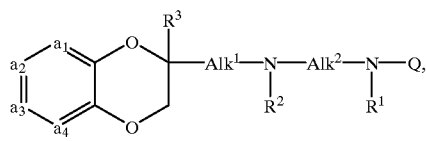

(I)

a N-oxide form, a pharmaceutically acceptable acid addition salt or a stereochemically isomeric form thereof, wherein $=a_1-a_2=a_3-a_4=$ is a bivalent radical of formula:

$=N-CH=CH-CH=$ (a), $=CH-N=CH-CH=$ (b), $=CH-CH=N-CH=$ (c), $=CH-CH=CH-N=$ (d), wherein one or two hydrogen atoms can be substituted by halo, hydroxy, $C_{1-6}$alkyl or $C_{1-6}$alkyloxy;

$R^1$, $R^2$ and $R^3$ each independently are hydrogen or $C_{1-6}$alkyl;

$Alk^1$ is $C_{1-5}$alkanediyl;

$Alk^2$ is $C_{2-15}$alkanediyl;

Q is a radical of formula

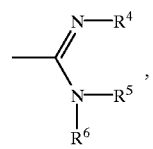 (aa)

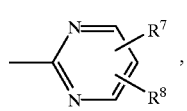 (bb)

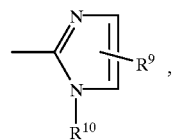 (cc)

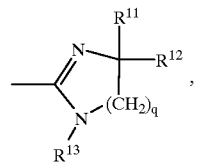 (dd)

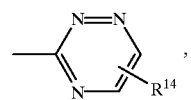 (ee)

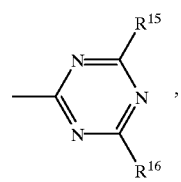 (ff)

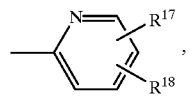 (gg)

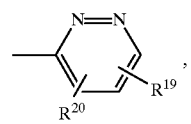 (hh)

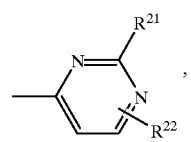 (ii)

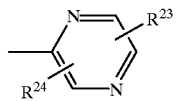 (jj)

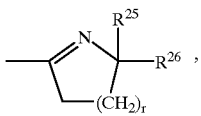 (kk)

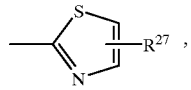 (ll)

wherein $R^4$ is hydrogen, cyano, aminocarbonyl or $C_{1-6}$alkyl;
$R^5$ is hydrogen, $C_{1-6}$alkyl, $C_{3-6}$alkenyl or $C_{3-6}$alkynyl;
$R^6$ is hydrogen or $C_{1-6}$alkyl; or $R^5$ and $R^6$ taken together may form a bivalent radical of formula —(CH$_2$)$_4$— or —(CH$_2$)$_5$—;

$R^7$ and $R^8$ each independently are hydrogen, hydroxy, halo, C$_{1-6}$alkyl, C$_{1-6}$alkyloxy, aryloxy, C$_{1-6}$alkylthio, cyano, amino, mono- or di(C$_{1-6}$alkyl)amino, mono- or di(C$_{3-6}$cycloalkyl)amino, aminocarbonyl, C$_{1-6}$alkyloxycarbonylamino, C$_{1-6}$alkylaminocarbonylamino, piperidinyl, pyrrolidinyl;

$R^9$ is hydrogen, hydroxy, halo, C$_{1-6}$alkyl, C$_{1-6}$alkyloxy, aryloxy, C$_{1-6}$alkylthio, cyano, amino, mono- or di(C$_{1-6}$alkyl)amino, mono- or di(C$_{3-6}$cycloalkyl)amino, aminocarbonyl, C$_{1-6}$alkyloxycarbonylamino, C$_{1-6}$alkylaminocarbonylamino, piperidinyl, pyrrolidinyl;

$R^{10}$ is hydrogen, C$_{1-6}$alkyl, C$_{1-6}$alkylcarbonyl, or arylC$_{1-6}$alkyl;

$R^{11}$ and $R^{12}$ are hydrogen or taken together with the carbon atom to which they are connected form C(O);

q is 1 or 2;

$R^{13}$ is hydrogen, C$_{1-6}$alkyl, C$_{1-6}$alkylcarbonyl, or arylC$_{1-6}$alkyl;

$R^{14}$ is hydrogen, hydroxy, halo, C$_{1-6}$alkyl, C$_{1-6}$alkyloxy, aryloxy, C$_{1-6}$alkylthio, cyano, amino, mono- or di(C$_{1-6}$alkyl)amino, mono- or di(C$_{3-6}$cycloalkyl)amino, aminocarbonyl, C$_{1-6}$alkyloxycarbonylamino, C$_{1-6}$alkylaminocarbonylamino, piperidinyl, pyrrolidinyl;

$R^{15}$ and $R^{16}$ each independently are hydrogen, hydroxy, halo, C$_{1-6}$alkyl, C$_{1-6}$alkyloxy, aryloxy, C$_{1-6}$alkylthio, cyano, amino, mono- or di(C$_{1-6}$alkyl)amino, mono- or di(C$_{3-6}$cycloalkyl)amino, aminocarbonyl, C$_{1-6}$alkyloxycarbonylamino, C$_{1-6}$alkylaminocarbonylamino, piperidinyl, pyrrolidinyl;

$R^{17}$ and $R^{18}$ each independently are hydrogen, hydroxy, halo, C$_{1-6}$alkyl, C$_{1-6}$alkyloxy, aryloxy, C$_{1-6}$alkylthio, cyano, amino, mono- or di(C$_{1-6}$alkyl)amino, mono- or di(C$_{3-6}$cycloalkyl)amino, aminocarbonyl, C$_{1-6}$alkyloxycarbonylamino, C$_{1-6}$alkylaminocarbonylamino, piperidinyl, pyrrolidinyl;

$R^{19}$ and $R^{20}$ each independently are hydrogen, hydroxy, halo, C$_{1-6}$alkyl, C$_{1-6}$alkyloxy, aryloxy, C$_{1-6}$alkylthio, cyano, amino, mono- or di(C$_{1-6}$alkyl)amino, mono- or di(C$_{3-6}$cycloalkyl)amino, aminocarbonyl, C$_{1-6}$alkyloxycarbonylamino, C$_{1-6}$alkylaminocarbonylamino, piperidinyl, pyrrolidinyl;

$R^{21}$ and $R^{22}$ each independently are hydrogen, hydroxy, halo, C$_{1-6}$alkyl, C$_{1-6}$alkyloxy, aryloxy, C$_{1-6}$alkylthio, cyano, amino, mono- or di(C$_{1-6}$alkyl)amino, mono- or di(C$_{3-6}$cycloalkyl)amino, aminocarbonyl, C$_{1-6}$alkyloxycarbonylamino, C$_{1-6}$alkylaminocarbonylamino, piperidinyl, pyrrolidinyl;

$R^{23}$ and $R^{24}$ each independently are hydrogen, hydroxy, halo, C$_{1-6}$alkyl, C$_{1-6}$alkyloxy, aryloxy, C$_{1-6}$alkylthio, cyano, amino, mono- or di(C$_{1-6}$alkyl)amino, mono- or di(C$_{3-6}$cycloalkyl)amino, aminocarbonyl, C$_{1-6}$alkyloxycarbonylamino, C$_{1-6}$alkylaminocarbonylamino, piperidinyl, pyrrolidinyl;

r is 1 or 2;

$R^{25}$ and $R^{26}$ are hydrogen or taken together with the carbon atom to which they are connected form a C(O);

$R^{27}$ is hydrogen, halo or C$_{1-6}$alkyl, and aryl is phenyl optionally substituted with halo, hydroxy, C$_{1-6}$alkyl or C$_{1-6}$alkyloxy.

2. A compound as claimed in claim 1, wherein $R^1$ and $R^2$ both are hydrogen and Alk$^2$ is 1,3-propanediyl.

3. A compound as claimed in claim 2, wherein "=a$_1$—a$_2$=a$_3$—a$_4$=" is a bivalent radical of formula (a) or (d).

4. A compound as claimed in any one of claims 1 to 3, wherein Q is a radical of formula (bb) or (hh).

5. A compound according to claim 1 wherein the compound is

N-[(2,3-dihydro-1,4-dioxino[2,3-b]pyridin-3-yl)methyl]-N'-2-pyrimidinyl-1,3-propanediamine;

N-[(2,3-dihydro-1,4-dioxino[2,3-b]pyridin-2-yl)methyl]-N'-2-pyrimidinyl-1,3-propanediamine;

N-(6-chloro-3-pyridazinyl)-N'-[(2,3-dihydro-1,4-dioxino[2,3-b]pyridin-2yl)methyl]-1,3-propanediamine; a pharmaceutically acceptable acid addition salt or a stereochemically isomeric form thereof.

6. A pharmaceutical composition containing a pharmaceutically acceptable carrier and as an active ingredient a therapeutically effective amount of a compound according to claim 1.

7. An intermediate of formula

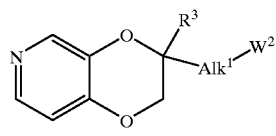

(III-b)

wherein one or two hydrogen attoms of the pyridine moiety can be substituted by halo, hydroxy, C$_{1-6}$alkyl or C$_{1-6}$alkyloxy; $R^3$ is hydrogen or C$_{1-6}$alkyl, Alk$^1$ is C$_{1-5}$alkanediyl, and W$^2$ is a reactive leaving group, an acid addition salt thereof or a stereochemically isomeric form thereof.

8. An intermediate of formula

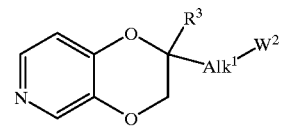

(III-c)

wherein one or two hydrogen attoms of the pyridine moiety can be substituted by halo, hydroxy, C$_{1-6}$alkyl or C$_{1-6}$alkyloxy; $R^3$ is hydrogen or C$_{1-6}$alkyl, Alk$^1$ is C$_{1-5}$alkanediyl, and W$^2$ is a reactive leaving group, an acid addition salt thereof or a stereochemically isomeric form thereof.

9. A process for preparing a compound as claimed in claim 1, comprising a) reacting an intermediate of formula (III), wherein "=a$_1$—a$_2$=a$_3$—a$_4$=", $R^3$ and Alk$^1$ are as defined in claim 1 and W$^2$ is a reactive leaving group, with an intermediate of formula (II), wherein $R^1$, $R^2$, Alk$^2$ and Q are as defined in claim 1;

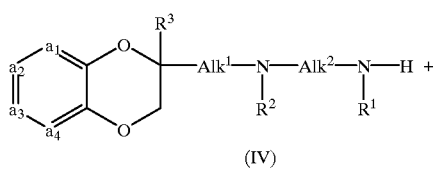

(IV)

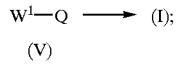

b) reacting an interemediate of formula (IV), wherein $=a_1-a_2=a_3-a_4=$, $R_1$, $R^2$, $R^3$, $Alk^1$ and $Alk^2$ are as defined in claim 1, with an intermediate of formula (V), wherein Q is as defined in claim 1 and $W^1$ is a reactive leaving group;

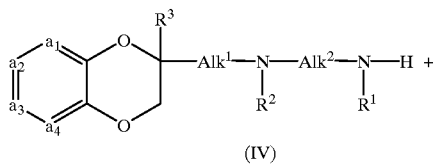

(IV)

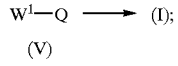

c) reductively N-alkylating an intermediate of formula (VIII), wherein $R^1$, $R^2$, $Alk^2$ and Q are as defined in claim 1, with an aldehyde of formula (VII) wherein "$=a_1-a_2=a_3-a_4=$" and $R^3$ are as defined in claim 1, $Alk^3$ is a direct bond or $C_{1-4}$alkanediyl;

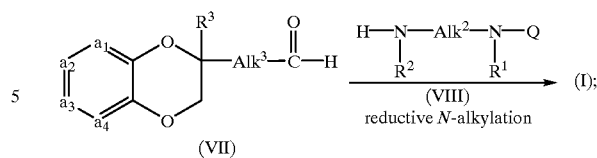

or optionally converting the compounds of formula (I) into each other following art-known functional group transformation reactions, and further, if desired, converting the compounds of formula (I) into a salt form by treatment with a pharmaceutically acceptable acid, or conversely, converting the salt form into the free base by treatment with alkali; and/or preparing stereochemically isomeric forms thereof.

10. A method for treating conditions related to vasodilation in patients in need of the same, which comprises administering to said patients an effective amount of a compound of claim 1.

11. A method for treating cephalic pain in patients in need of the same, which comprises administering to said patients an effective amount of a compound of claim 1.

12. A method for treating migraine in patients in need of the same, which comprises administering to said patients an effective amount of a compound of claim 1.

13. A method of treating conditions selected from the group consisting of cluster headache and headache associated with vascular disorders in patients in need of same, which comprises administrating to said patients an effective amount of a compound of claim 1.

14. A method for treating migraine in patients in need of the same, which comprises administering to said patients an effective amount of a compound of claim 2.

* * * * *